United States Patent
Etou et al.

(10) Patent No.: US 12,404,223 B2
(45) Date of Patent: Sep. 2, 2025

(54) METHOD FOR PRODUCING ALKANE COMPOUND

(71) Applicant: DAIKIN INDUSTRIES, LTD., Osaka (JP)

(72) Inventors: Yuusuke Etou, Osaka (JP); Shingo Nakamura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 665 days.

(21) Appl. No.: 17/825,504

(22) Filed: May 26, 2022

(65) Prior Publication Data

US 2022/0289649 A1    Sep. 15, 2022

Related U.S. Application Data

(63) Continuation of application No. PCT/JP2020/043536, filed on Nov. 24, 2020.

(30) Foreign Application Priority Data

Nov. 27, 2019   (JP) ................. 2019-213925

(51) Int. Cl.
  *C07C 17/354*   (2006.01)
(52) U.S. Cl.
  CPC ................ *C07C 17/354* (2013.01)
(58) Field of Classification Search
  CPC ..... C07C 17/354; C07C 17/281; C07C 19/08; C07B 2200/07; C07B 35/02
  See application file for complete search history.

(56) References Cited

U.S. PATENT DOCUMENTS 2,404,374 A    7/1946    Harmon

FOREIGN PATENT DOCUMENTS

JP    11-106356    4/1999

OTHER PUBLICATIONS

Donald Bethell et al., "Chemically Induced Dynamic Polarisation of $^{19}$F Nuclei in the Dimerisation of α-Fluorobenzyl Radicals", Journal of the Chemical Society, pp. 603-606, Jan. 1, 1979.

Extended European Search Report issued Dec. 12, 2023 in corresponding European Patent Application No. 20893616.1.
International Search Report issued Jan. 26, 2021 in International (PCT) Application No. PCT/JP2020/043536.
Hudlicky et al., "Practical preparation of some potentially anesthetic fluoroalkanes: regiocontrolled introduction of hydrogen atoms", Journal of Fluorine Chemistry, 1992, vol. 59, pp. 9-14.
Arai, "Analysis of heterogeneous hydrogenation reactions by gas-phase of $^{19}$F-NMR", Catalysts & catalysis, 1998, vol. 40, No. 3, pp. 199-200, with English translation.
P.M. Kating et al., "Hydrogenation of Fluoroolefins Studied by Gas Phase NMR: A New Technique for Heterogeneous Catalysis", Journal of the American Chemical Society, 1996, vol. 118, pp. 10000-10001.

*Primary Examiner* — Jafar F Parsa
(74) *Attorney, Agent, or Firm* — Wenderoth, Lind & Ponack, L.L.P.

(57) ABSTRACT

In the presence of a catalyst and a cycloalkane compound represented by formula (3):

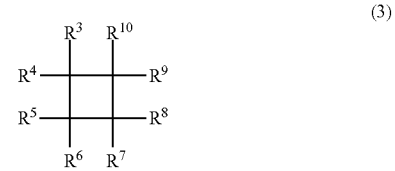

wherein $R^3$, $R^4$, $R^5$, $R^6$, $R^7$, $R^8$, $R^9$, and $R^{10}$ are the same or different and each is a halogen atom, an alkyl group, or a fluoroalkyl group; an alkene compound represented by formula (2):

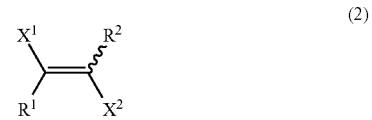

wherein $X^1$, $X^2$, $R^1$, and $R^2$ are as defined above; is reacted with a hydrogen-containing gas to hydrogenate the alkene compound represented by formula (2), whereby an alkane compound represented by $R^1CHX^1CHX^2R^2$, wherein $X^1$ and $X^2$ are the same or different and each is a halogen atom, and $R^1$ and $R^2$ are the same or different and each is an alkyl group or a fluoroalkyl group; can be synthesized in such a manner that (S),(R)-isomer, (R),(R)-isomer, and (S),(S)-isomer are co-produced.

11 Claims, No Drawings

METHOD FOR PRODUCING ALKANE COMPOUND

TECHNICAL FIELD

The present disclosure relates to a method for producing an alkane compound.

BACKGROUND ART

As a method for synthesizing $CF_3CHFCHFCF_3$, which is a halogenated alkane compound, for example, it is known to perform a hydrogenation reaction of perfluoro-2-butene, as described in NPL 1. $CF_3CHFCHFCF_3$ has 3 isomers, i.e., (S),(R) isomer, (R),(R) isomer, and (S),(S) isomer, shown below; however, most $CF_3CHFCHFCF_3$ obtained by the above synthesis method is (S),(R) isomer.

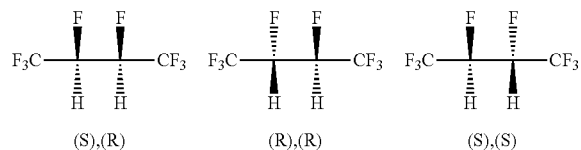

CITATION LIST

Non-Patent Literature

NPL 1: Journal of Fluorine Chemistry, 1992, Vol. 59, pp. 9-14

SUMMARY

Item 1. A method for producing an alkane compound represented by formula (1):

$$R^1CHX^1CHX^2R^2 \quad (1)$$

wherein $X^1$ and $X^2$ are the same or different and each is a halogen atom, and $R^1$ and $R^2$ are the same or different and each is an alkyl group or a fluoroalkyl group; the method comprising:

(IIA) reacting, in the presence of a catalyst and a cycloalkane compound represented by formula (3):

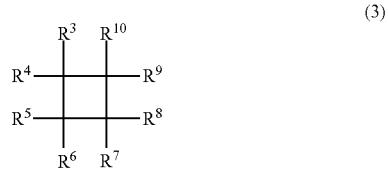

wherein $R^3$, $R^4$, $R^5$, $R^6$, $R^7$, $R^8$, $R^9$, and $R^{10}$ are the same or different and each is a halogen atom, an alkyl group, or a fluoroalkyl group; an alkene compound represented by formula (2):

wherein $X^1$, $X^2$, $R^1$, and $R^2$ are as defined above; and a hydrogen-containing gas to hydrogenate the alkene compound represented by formula (2).

Advantageous Effects of Invention

According to the present disclosure, an alkane compound represented by $R^1CHX^1CHX^2R^2$ can be synthesized in such a manner that (S),(R) isomer, (R),(R) isomer, and (S),(S) isomer are co-produced.

DESCRIPTION OF EMBODIMENTS

In the present specification, the term "comprise" is a concept including "comprising," "consisting essentially of," and "consisting of." In the present specification, the numerical range indicated by "A to B" means A or more and B or less.

In the present disclosure, "selectivity" means the ratio (mol %) of the total molar amount of the target compound contained in the effluent gas from the reactor outlet, based on the total molar amount of compounds other than the raw material compound in the effluent gas.

In the present disclosure, "conversion rate" means the ratio (mol %) of the total molar amount of compounds other than the raw material compound contained in the effluent gas from the reactor outlet, based on the molar amount of the raw material compound supplied to the reactor.

Conventionally, in NPL 1, $CF_3CHFCHFCF_3$ was synthesized by performing a hydrogenation reaction of 1,1,1,4,4,4-hexafluoro-2-butene; however, most isomers that could be synthesized were (S),(R) isomer alone. This is because a hydrogen addition reaction using a catalyst is known to be syn addition, and an anti addition reaction in which two hydrogen atoms are added from opposite directions is unlikely to occur. That is, according to the conventional method, isomers other than (S)(R) isomer could hardly be synthesized. On the other hand, according to the production method of the present disclosure, an alkane compound represented by $R^1CHX^1CHX^2R^2$ can be synthesized in such a manner that (S),(R) isomer, (R),(R) isomer, and (S),(S) isomer are co-produced. Not only (S),(R) isomer, but also (R),(R) isomer and (S),(S) isomer can be co-produced, whereby building blocks with the desired optical activity can be obtained.

1. Method for Producing Alkane Compound 1-1: Method for Producing Alkane Compound from Alkene Compound The method for producing an alkane compound of the present disclosure is a method for producing an alkane compound represented by formula (1):

$$R^1CHX^1CHX^2R^2 \quad (1)$$

wherein $X^1$ and $X^2$ are the same or different and each is a halogen atom, and $R^1$ and $R^2$ are the same or different and each is an alkyl group or a fluoroalkyl group; the method comprising:

(IIA) reacting, in the presence of a catalyst and a cycloalkane compound represented by formula (3):

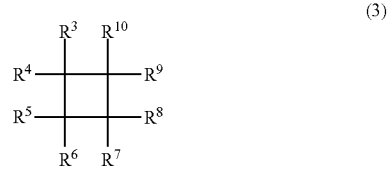

wherein $R^3$, $R^4$, $R^5$, $R^6$, $R^7$, $R^8$, $R^9$, and Rao are the same or different and each is a halogen atom, an alkyl group, or a fluoroalkyl group, provided that when $R^1$ and $R^2$ in formula (1) are both alkyl groups, $R^3$, $R^4$, $R^5$, $R^6$, $R^7$, $R^8$, $R^9$, and $R^{10}$ are the same or different and each is a halogen atom or a fluoroalkyl group; an alkene compound represented by formula (2):

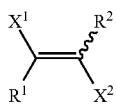

(2)

wherein $X^1$, $X^2$, $R^1$, and $R^2$ are as defined above; and a hydrogen-containing gas to hydrogenate the alkene compound represented by formula (2).

According to the present disclosure, the cycloalkane compound represented by formula (3) described above inhibits part of a syn addition reaction in which two hydrogen atoms are added to the alkene compound represented by formula (2) from the same direction, and an anti addition reaction in which two hydrogen atoms are added from opposite directions is more likely to occur. As a result, the alkane compound represented by formula (1) can be synthesized in such a manner that (S),(R) isomer, (R),(R) isomer, and (S),(S) isomer are co-produced.

(1-1-1) Raw Material Compound (Alkene Compound)

The alkene compound as a raw material compound that can be used in the production method of the present disclosure is, as described above, an alkene compound represented by formula (2):

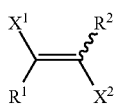

(2)

wherein $X^1$ and $X^2$ are the same or different and each is a halogen atom, and $R^1$ and $R^2$ are the same or different and each is an alkyl group or a fluoroalkyl group.

The alkene compound represented by formula (2) includes both alkene compounds represented by formulas (2A) and (2B):

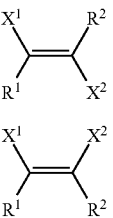

(2A)

(2B)

wherein $X^1$, and $R^2$ are as defined above.

In formula (2), examples of the halogen atom represented by $X^1$ and $X^2$ include a fluorine atom, a chlorine atom, a bromine atom, and an iodine atom.

In formula (2), examples of the alkyl group represented by $R^1$ and $R^2$ include alkyl groups having 1 to 20 carbon atoms, preferably 1 to 12 carbon atoms, more preferably 1 to 6 carbon atoms, and even more preferably 1 to 3 carbon atoms, such as methyl, ethyl, n-propyl, and isopropyl groups.

In formula (2), the fluoroalkyl group represented by $R^1$ and $R^2$ is, for example, a fluoroalkyl group (in particular, a perfluoroalkyl group) having 1 to 20 carbon atoms, preferably 1 to 12 carbon atoms, more preferably 1 to 6 carbon atoms, and even more preferably 1 to 3 carbon atoms, such as trifluoromethyl and pentafluoroethyl groups.

Of these, $X^1$ and $X^2$ are preferably fluorine atoms, from the viewpoint of the conversion rate of the reaction, and the selectivity and yield of the target alkane compound ((S),(R) isomer, (R),(R) isomer, and (S),(S) isomer).

Further, $R^1$ and $R^2$ are preferably fluoroalkyl groups, and more preferably perfluoroalkyl groups, from the viewpoint of the conversion rate of the reaction, and the selectivity and yield of the target alkane compound ((S),(R) isomer, (R),(R) isomer, and (S),(S) isomer).

$X^1$, $X^2$, $R^1$, and $R^2$ may be the same or different.

Specific examples of the alkene compound represented by formula (2) as a raw material compound that satisfies the above conditions include the following:

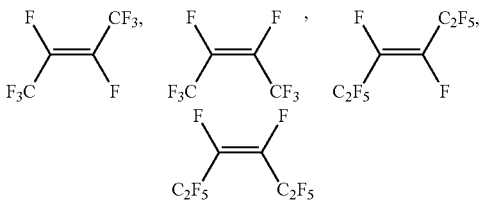

These alkene compounds represented by formula (2) can be used singly or in combination of two or more. Such alkene compounds represented by formula (2) may be known or commercial products, or may be synthesized for use. The production method in the case of synthesizing the alkene compound represented by formula (2) is described later.

(1-1-2) Hydrogen Addition Reaction

In the method for producing an alkane compound from an alkene compound in the present disclosure, for example, in the alkene compound represented by formula (2) as a raw material compound, $X^1$ and $X^2$ are preferably fluorine atoms, and $R^1$ and $R^2$ are preferably fluoroalkyl groups, more perfluoroalkyl groups, and particularly preferably trifluoromethyl groups, from the viewpoint of the conversion rate of the reaction, and the selectivity and yield of the target alkane compound ((S),(R) isomer, (R), (R) isomer, and (S),(S) isomer).

That is, preferred is a hydrogen addition reaction (syn addition and anti addition reactions) according to the following reaction formula:

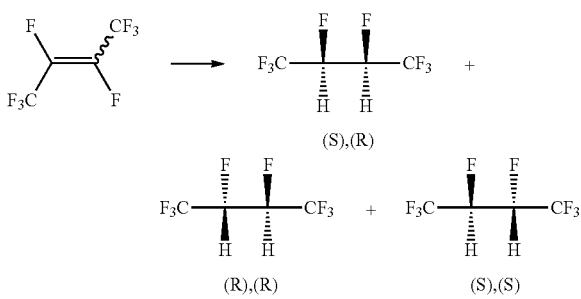

The step of subjecting the alkene compound represented by formula (2) to a hydrogen addition reaction to obtain the alkane compound represented by formula (1) in the present disclosure is preferably carried out in the gas phase, in the case of performing the hydrogen addition reaction continuously after the method for producing the alkene compound represented by formula (2) described later, and from the viewpoint of productivity. When the step of subjecting the alkene compound represented by formula (2) to a hydrogen addition reaction to obtain the alkane compound represented by formula (1) in the present disclosure is carried out in the gas phase, there are advantages in that the hydrogen addition reaction can be performed continuously after the method for producing the alkene compound represented by formula (2) described later, there is no need to use a solvent, industrial waste does not occur, and excellent productivity is achieved.

The step of subjecting the alkene compound represented by formula (2) to a hydrogen addition reaction to obtain the alkane compound represented by formula (1) in the present disclosure is preferably carried out in the gas phase, particularly by a gas-phase continuous flow process using a fixed bed reactor. When a gas-phase continuous flow process is used, the device, operation, etc. can be simplified, and it is economically advantageous.

(1-1-3) Cycloalkane Compound Represented by Formula (3)

The step of subjecting the alkene compound represented by formula (2) to a hydrogen addition reaction to obtain the alkane compound represented by formula (1) in the present disclosure is performed in the presence of a cycloalkane compound represented by formula (3):

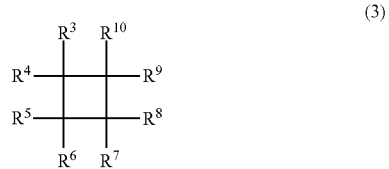

wherein $R^3$, $R^4$, $R^5$, $R^6$, $R^7$, $R^9$, and $R^{10}$ are the same or different and each is a halogen atom, an alkyl group, or a fluoroalkyl group.

The cycloalkane compound represented by formula (3) inhibits part of a syn addition reaction in which two hydrogen atoms are added to the alkene compound represented by formula (2) from the same direction, and an anti addition reaction in which two hydrogen atoms are added from opposite directions is more likely to occur. As a result, the alkane compound represented by formula (1) can be synthesized in such a manner that (S),(R) isomer, (R),(R) isomer, and (S),(S) isomer are co-produced.

In formula (3), the halogen atom, alkyl group, and fluoroalkyl group represented by $R^3$, $R^4$, $R^5$, $R^6$, $R^7$, $R^8$, $R^9$, and $R^{10}$ can be the same as those described above. The same applies to preferred specific examples.

However, according to the method for producing the alkene compound represented by formula (2) described later, it can be produced as a mixture comprising the alkene compound represented by formula (2) and the cycloalkane compound represented by formula (3); however, when $R^1$ and $R^2$ are both alkyl groups, if $R^3$, $R^4$, $R^5$, $R^6$, $R^7$, $R^8$, $R^9$, and $R^{10}$ are also alkyl groups, the alkene compound represented by formula (2) cannot be obtained. Therefore, when the production method described later is used as the method for producing the alkene compound represented by formula (2), which is a raw material compound, and when $R^1$ and $R^2$ are both alkyl groups, $R^3$, $R^4$, $R^5$, $R^6$, $R^7$, $R^8$, $R^9$, and $R^{10}$ are preferably halogen atoms or fluoroalkyl groups.

$R^3$, $R^4$, $R^5$, $R^6$, $R^7$, $R^8$, $R^9$, and $R^{10}$ are preferably halogen atoms or fluoroalkyl groups, more preferably halogen atoms, and even more preferably fluorine atoms, from the viewpoint of the conversion rate of the reaction, and the selectivity and yield of the target alkane compound ((S),(R) isomer, (R),(R) isomer, and (S), (S) isomer).

Specific examples of the cycloalkane compound represented by formula (3) that satisfies the above conditions include the following:

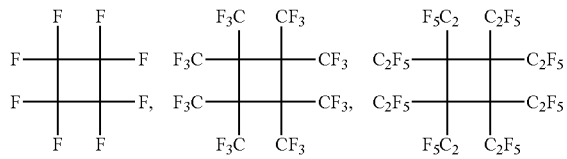

In the production method of the present disclosure, when the alkene compound represented by formula (2) is subjected to a hydrogen addition reaction in the presence of the cycloalkane compound represented by formula (3) and a catalyst, it is preferable, for example, to bring the cycloalkane compound represented by formula (3) in the form of gas (gas phase) into contact with the alkene compound represented by formula (2).

In the production method of the present disclosure, when the alkene compound represented by formula (2) is subjected to a hydrogen addition reaction in the presence of the cycloalkane compound represented by formula (3) and a catalyst, the amount of the cycloalkane compound represented by formula (3) used is not limited. From the viewpoint of the conversion rate of the reaction, and the selectivity and yield of the target alkane compound ((S),(R) isomer, (R),(R) isomer, and (S),(S) isomer), it is preferably 0.5 to 20 mol, more preferably 0.7 to 15 mol, and even more preferably 0.8 to 10 mol, per mol of the alkene compound represented by formula (2), which is a raw material compound.

(1-1-4) Catalyst

The step of subjecting the alkene compound represented by formula (2) to a hydrogen addition reaction to obtain the alkane compound represented by formula (1) in the present disclosure is performed in the presence of a catalyst.

The metal species that constitute the catalyst are preferably transition metal elements belonging to groups 8 to 11 of the periodic table, and more preferably transition metal elements belonging to groups 9 to 10 of the periodic table. Specific examples of such metal species include platinum, palladium, rhodium, nickel, and the like. The catalyst of the present disclosure may contain such a metal alone, may be a porous metal catalyst, or may contain such a metal as a compound with other elements. Usable examples include alloys of catalytic metal species, such as platinum, palladium, rhodium, and nickel, and non-catalytic metal species, such as aluminum, silicon, magnesium, and zinc, catalysts in which the non-catalytic metal species are eluted from such alloys using an acid or alkaline solution (Raney catalysts), $Pt(PtO_2)$, Adams' catalyst ($PtO_2$—$H_2O$), colloidal palladium, colloidal platinum, platinum black, and the like. These can be used singly or in combination of two or more.

Further, in the present disclosure, the metal species mentioned above can be directly used as catalysts, or can be supported on a carrier for use. The carrier that can be used in this case is not limited, and examples include carbon, alumina ($Al_2O_3$), zirconia ($ZrO_2$), silica ($SiO_2$), titania ($TiO_2$), and the like. Of these, carbon, alumina, etc. are preferred, and carbon is more preferred, from the viewpoint of the conversion rate of the reaction, and the selectivity and yield of the target alkane compound ((S),(R) isomer, (R),(R) isomer, and (S), (S) isomer). As carbon, activated carbon, amorphous carbon, graphite, diamond, or the like can be used.

In the production method of the present disclosure, when the alkene compound represented by formula (2) is subjected to a hydrogen addition reaction in the presence of the cycloalkane compound represented by formula (3) and a catalyst, it is preferable to, for example, bring the catalyst in a solid state (solid phase) into contact with the alkene compound represented by formula (2). In this case, the shape of the catalyst may be powder; however, pellets are preferable when they are used for a gas-phase continuous flow process reaction.

The specific surface area of the catalyst measured by the BET method (hereinafter also referred to as "BET specific surface area") is generally preferably 10 to 3000 $m^2/g$, more preferably 10 to 2500 $m^2/g$, even more preferably 20 to 2000 $m^2/g$, and particularly preferably 30 to 1500 $m^2/g$, from the viewpoint of the conversion rate of the reaction, and the selectivity and yield of the target alkane compound ((S),(R) isomer, (R),(R) isomer, and (S),(S) isomer).

(1-1-5) Hydrogen-Containing Gas

Examples of the hydrogen-containing gas include a hydrogen gas, as well as mixtures of a hydrogen gas and other gases (e.g., a mixed gas of hydrogen and an inert gas such as nitrogen or argon mixed at any ratio, and oxyhydrogen, which is a mixed gas of oxygen and hydrogen). However, since the production method of the present disclosure employs a hydrogen addition reaction, it is preferable that hydrogen halide (hydrogen fluoride) etc. are not contained or are present in a very small amount (e.g., 5 volume % or less based on the total amount of the hydrogen-containing gas) as the hydrogen-containing gas. From the viewpoint of the conversion rate of the reaction, and the selectivity and yield of the target alkane compound ((S),(R) isomer, (R),(R) isomer, and (S),(S) isomer), it is preferable to use a hydrogen gas. These hydrogen-containing gases can be used singly or in combination of two or more.

It is generally preferable to supply the hydrogen-containing gas in a vapor state together with the alkene compound represented by formula (2) (raw material compound) into a reactor. The amount of the hydrogen-containing gas supplied is preferably 0.7 to 10 mol, more preferably 0.8 to 5 mol, and even more preferably 0.9 to 3 mol, per mol of the alkene compound represented by formula (2) (raw material compound), from the viewpoint of the conversion rate of the reaction, and the selectivity and yield of the target alkane compound ((S),(R) isomer, (R),(R) isomer, and (S),(S) isomer).

(1-1-6) Reaction Temperature

In the step of subjecting the alkene compound represented by formula (2) (raw material compound) to a hydrogen addition reaction in the present disclosure, the reaction temperature is generally 20 to 400° C., more preferably 30 to 300° C., and even more preferably 40 to 200° C., from the viewpoint of the conversion rate of the reaction, and the selectivity and yield of the target alkane compound ((S),(R) isomer, (R),(R) isomer, and (S),(S) isomer).

(1-1-7) Reaction Time

In the step of subjecting the alkene compound represented by formula (2) (raw material compound) to a hydrogen addition reaction in the present disclosure, for example, when using a gas-phase flow process, the contact time of the raw material compound with the catalyst (W/F) [W: weight (g) of catalyst, F: flow rate (cc/sec) of raw material compound] is preferably 0.5 to 50 g·sec/cc, more preferably 1 to 40 g·sec/cc, and even more preferably 1.5 to 30 g·sec/cc, from the viewpoint of the conversion rate of the reaction, and the selectivity and yield of the target alkane compound ((S),(R) isomer, (R),(R) isomer, and (S),(S) isomer). The contact time refers to the time of contact between the raw material compound and the catalyst, namely reaction time.

(1-1-8) Reaction Pressure

In the step of subjecting the alkene compound represented by formula (2) (raw material compound) to a hydrogen addition reaction in the present disclosure, the reaction pressure is preferably 0 kPa or more, more preferably 10 kPa or more, even more preferably 20 kPa or more, and particularly preferably 30 kPa or more, from the viewpoint of the conversion rate of the reaction, and the selectivity and yield of the target alkane compound ((S),(R) isomer, (R),(R) isomer, and (S),(S) isomer). The upper limit of the reaction pressure is not limited, and is generally about 2 MPa. In the present disclosure, the pressure is gauge pressure unless otherwise specified.

In the step of subjecting the alkene compound represented by formula (2) (raw material compound) to a hydrogen addition reaction in the present disclosure, the reactor for reacting the alkene compound represented by formula (2) (raw material compound), the cycloalkane compound represented by formula (3), and a catalyst is not limited in its shape and structure as long as it can withstand the temperature and pressure described above. Examples of the reactor include a vertical reactor, a horizontal reactor, a multitubular reactor, and the like. Examples of the material of the reactor include glass, stainless steel, iron, nickel, iron-nickel alloys, and the like.

(1-1-9) Example of Hydrogen Addition Reaction

The step of subjecting the alkene compound represented by formula (2) (raw material compound) to a hydrogen addition reaction in the present disclosure can be carried out in a batch mode or a flow mode in which the alkene compound represented by formula (2) as the raw material compound is continuously fed into the reactor and the alkane compound represented by formula (1) as the target compound is continuously withdrawn from the reactor. The step of subjecting the alkene compound represented by formula (2) (raw material compound) to a hydrogen addition reaction in the present disclosure is preferably carried out in the gas phase, particularly by a gas-phase continuous flow process using a fixed bed reactor. When a gas-phase continuous flow process is used, the device, operation, etc. can be simplified, and it is economically advantageous.

The atmosphere when the alkene compound represented by formula (2) (raw material compound) is subjected to a hydrogen addition reaction in the present disclosure is preferably an inert gas atmosphere, a hydrogen gas atmosphere, or the like, in terms of suppressing the deterioration of the catalyst. Examples of the inert gas include nitrogen, helium, argon, and the like. Among these inert gases, nitrogen is preferable from the viewpoint of cost reduction. The concentration of the inert gas is preferably 0 to 50 mol % of the gas component introduced into the reactor.

After the completion of the hydrogen addition reaction, if necessary, purification treatment can be performed according to a general method to thereby obtain the alkane compound represented by formula (1).

(1-1-10) Target Compound (Alkane Compound)

The thus-obtained target compound of the present disclosure is an alkane compound represented by formula (1):

$$R^1CHX^1CHX^2R^2 \tag{1}$$

wherein $X^1$ and $X^2$ are the same or different and each is a halogen atom, and $R^1$ and $R^2$ are the same or different and each is an alkyl group or a fluoroalkyl group.

$X^1$, $X^2$, and $R^2$ in formula (2A) correspond, respectively, to $X^1$, $X^2$, $R^1$ and $R^2$ in formula (2) described above. Therefore, examples of the alkane compound represented by formula (1) to be produced include $CHF_2CHF_2$, $CF_3CHFCHFCF_3$, $C_2F_5CHFCHFC_2F_5$, and the like. As described above, according to the conventional method, most of the obtained target products is (S),(R) isomer alone; however, according to the production method of the present disclosure, the alkane compound represented by formula (1) can be obtained in such a manner that (S),(R) isomer, (R),(R) isomer, and (S),(S) isomer are co-produced. That is, the target compounds include all of (S),(R) isomer, (R),(R) isomer, and (S),(S) isomer. Accordingly, examples of the obtained target compound include the following:

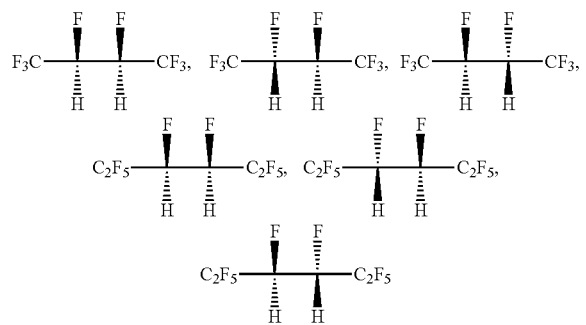

The contents of (S),(R) isomer, (R),(R) isomer, and (S),(S) isomer are described later. Each isomer is analyzed by gas chromatography (content) using a chiral column and NMR (structure determination).

The thus-obtained alkane compound represented by formula (1) can be effectively used for various applications, such as intermediates for organic synthesis, etching gases, and deposit gases. In particular, when the previously reported reaction is used for the alkane compound represented by formula (1), alkyne compounds ($CF_3CHCCF_3$ etc.) that can be effectively used for various applications, such as etching gases, cleaning gases, deposit gases, refrigerants, heat transfer media, and building blocks for organic synthesis, can also be synthesized.

1-2: Method for Producing Alkene Compound

In the production method of the present disclosure, the alkene compound represented by formula (2) used as a raw material compound may be a known or commercial product, or may be synthesized, as described above. For example, the alkene compound represented by formula (2) can be synthesized according to the methods described in Journal of the Chemical Society, 1953, pp. 2082-2084, U.S. Pat. No. 2,404,374B, etc.

When the alkene compound represented by formula (2) is synthesized, the production method thereof comprises, for example:

(IA) reacting a cycloalkane compound represented by formula (3):

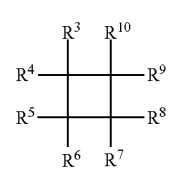

wherein $R^3$, $R^4$, $R^5$, $R^6$, $R^7$, $R^8$, $R^9$, and $R^{10}$ are as defined above, provided that when $R^1$ and $R^2$ in formula (1) are both alkyl groups, $R^3$, $R^4$, $R^5$, $R^6$, $R^7$, $R^8$, $R^9$, and $R^{10}$ are the same or different and each is a halogen atom or a fluoroalkyl group; and an alkene compound represented by formula (4):

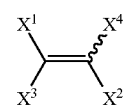

wherein $X^1$ and $X^2$ are as defined above, and $X^3$ and $X^4$ are the same or different and each is a halogen atom; to obtain an alkene compound represented by formula (2):

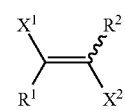

wherein $X^1$, $X^2$, $R^1$, and $R^2$ are as defined above.

(1-2-1) Raw Material Compound (Alkene Compound)

The alkene compound represented by formula (4) as a usable raw material compound is, as described above, an alkene compound represented by formula (4):

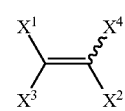

wherein $X^1$, $X^2$, $X^3$ and $X^4$ are the same or different and each is a halogen atom.

When there are cis and trans isomers, the alkene compound represented by formula (2) includes both alkene compounds represented by formulas (4A) and (4B):

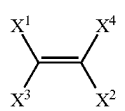

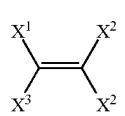

wherein $X^1$, $X^2$, and $X^4$ are as defined above.

In formula (4), the halogen atoms represented by $X^1$, $X^2$, and $X^4$ can be those mentioned above. The same applies to preferred specific examples. Of these, fluorine atoms are preferred, from the viewpoint of the conversion rate of the reaction, and the selectivity and yield of the target alkene compound represented by formula (2).

$X^1$, $X^2$, $X^3$, and $X^4$ may be the same or different.

Specific examples of the alkene compound represented by formula (4) as a raw material compound that satisfies the above conditions include the following:

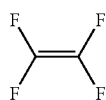

These alkene compounds represented by formula (4) can be used singly or in combination of two or more. Such alkene compounds represented by formula (4) may be known or commercial products.

(1-2-2) Cycloalkane Compound Represented by Formula (3)

For the cycloalkane compound represented by formula (3), the above explanation can be directly used.

(1-2-3) Thermal Decomposition Reaction

In the method for producing the alkane compound represented by formula (2) from the alkene compound represented by formula (4), for example, in the alkene compound represented by formula (4) as a raw material compound, $X^1$, $X^2$, $X^3$, and $X^4$ are preferably fluorine atoms, and $R^3$, $R^4$, $R^5$, $R^6$, $R^7$, $R^9$, and $R^{10}$ are also preferably halogen atoms, and more preferably fluorine atoms, from the viewpoint of the conversion rate of the reaction, and the selectivity and yield of the target alkene compound represented by formula (2).

That is, it is preferable to proceed the thermal decomposition reaction according to the following reaction formula:

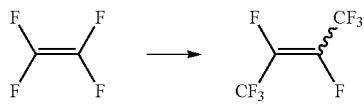

The step of obtaining the alkene compound represented by formula (2) from the alkene compound represented by formula (4) is preferably carried out in the gas phase, in the case of continuously producing the alkane compound represented by formula (1) by the hydrogen addition reaction described above after that step, and from the viewpoint of productivity. When the step of obtaining the alkene compound represented by formula (2) from the alkene compound represented by formula (4) is carried out in the gas phase, there are advantages in that the alkane compound represented by formula (1) can be continuously produced by the hydrogen addition reaction after that step, there is no need to use a solvent, industrial waste does not occur, and excellent productivity is achieved.

The step of obtaining the alkene compound represented by formula (2) from the alkene compound represented by formula (4) is preferably carried out in the gas phase, particularly by a gas-phase continuous flow process using a fixed bed reactor. When a gas-phase continuous flow process is used, the device, operation, etc. can be simplified, and it is economically advantageous.

(1-2-4) Reaction Temperature

In the step of obtaining the alkene compound represented by formula (2) from the alkene compound represented by formula (4), the reaction temperature is generally preferably 400 to 1000° C., more preferably 500 to 900° C., and even more preferably 600 to 800° C., from the viewpoint of the conversion rate of the reaction, and the selectivity and yield of the target alkene compound represented by formula (2).

(1-2-5) Reaction Time (Flow Rate)

In the step of obtaining the alkene compound represented by formula (2) from the alkene compound represented by formula (4), for example, when using a gas-phase flow process, the flow rate of the raw material compound is preferably 0.01 to 10 g/sec, more preferably 0.05 to 5 g/sec, and even mere preferably 0.1 to 1 g/sec, from the viewpoint of the conversion rate of the reaction, and the selectivity and yield of the target alkene compound represented by formula (2).

(1-2-6) Reaction Pressure

In the step of obtaining the alkene compound represented by formula (2) from the alkene compound represented by formula (4), the reaction pressure is preferably 0 kPa or more, more preferably 10 kPa or more, even more preferably 20 kPa or more, and particularly preferably 30 kPa or more, from the viewpoint of the conversion rate of the reaction, and the selectivity and yield of the target alkene compound represented by formula (2). The upper limit of the reaction pressure is not limited, and is generally about 2 MPa. In the present disclosure, the pressure is gauge pressure unless otherwise specified.

In the step of obtaining the alkene compound represented by formula (2) from the alkene compound represented by formula (4), the reactor for reacting the alkene compound represented by formula (4) (raw material compound) and the cycloalkane compound represented by formula (3) is not limited in its shape and structure as long as it can withstand the temperature and pressure described above. Examples of the reactor include a vertical reactor, a horizontal reactor, a multitubular reactor, and the like. Examples of the material of the reactor include glass, stainless steel, iron, nickel, iron-nickel alloys, and the like.

(1-2-7) Example of Thermal Decomposition Reaction

The step of obtaining the alkene compound represented by formula (2) from the alkene compound represented by formula (4) can be carried out in a batch mode or a flow mode in which the alkene compound represented by formula (4) as the raw material compound is continuously fed into the reactor and the alkene compound represented by formula (2) as the target compound is continuously withdrawn from the reactor. If the alkene compound represented by formula (2) as the target compound remains in the reactor, the side reaction can proceed further; thus, it is preferable to carry out the reaction in a flow mode.

The step of obtaining the alkene compound represented by formula (2) from the alkene compound represented by formula (4) is preferably carried out in the gas phase, particularly by a gas-phase continuous flow process using a fixed bed reactor. When a gas-phase continuous flow process is used, the device, operation, etc. can be simplified, and it is economically advantageous.

The atmosphere when obtaining the alkene compound represented by formula (2) from the alkene compound represented by formula (4) is preferably an inert gas atmosphere, from the viewpoint of suppressing impurities. Examples of the inert gas include nitrogen, helium, argon, and the like. Among these inert gases, nitrogen is preferable from the viewpoint of cost reduction. The concentration of the inert gas is preferably 0 to 50 mol % of the gas component introduced into the reactor.

After the completion of the hydrogen addition reaction, if necessary, purification treatment can be performed according to a general method to thereby obtain the alkene compound represented by formula (2).

(1-2-8) Target Compound (Alkene Compound)

The thus-obtained alkene compound represented by formula (2) is as explained above. That is, the above explanation can be used for the explanation of the obtained alkene compound represented by formula (2).

1-3: Method for Producing Alkane Compound Represented by Formula (1) from Alkene Compound Represented by Formula (4) via Alkene Compound Represented by Formula (2)

The method for producing an alkane compound of the present disclosure is a method for producing an alkane compound represented by formula (1):

$$R^1CHX^1CHX^2R^2 \quad (1)$$

wherein $X^1$ and $X^2$ are the same or different and each is a halogen atom, and $R^1$ and $R^2$ are the same or different and each is an alkyl group or a fluoroalkyl group; the method comprising:

(IB) reacting a cycloalkane compound represented by formula (3):

(3)

wherein $R^3$, $R^4$, $R^5$, $R^6$, $R^7$, $R^8$, $R^9$, and $R^{10}$ are the same or different and each is a halogen atom, an alkyl group, or a fluoroalkyl group, provided that when $R^1$ and $R^2$ in formula (1) are both alkyl groups, $R^3$, $R^4$, $R^5$, $R^6$, $R^7$, $R^8$, $R^9$, and $R^{10}$ are the same or different and each is a halogen atom or a fluoroalkyl group; and an alkene compound represented by formula (4):

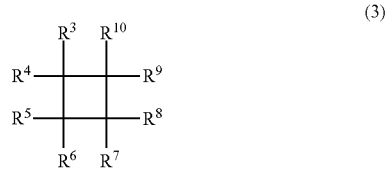

(4)

wherein $X^1$ and $X^2$ are as defined above, and $X^3$ and $X^4$ are the same or different and each is a halogen atom; to obtain a mixture comprising a cycloalkene compound represented by formula (2):

(2)

wherein $X^1$, and $R^2$ are as defined above; and the cycloalkane compound represented by formula (3); and (IIB) reacting the mixture obtained in step (IB) and a hydrogen-containing gas in the presence of a catalyst to hydrogenate the cycloalkene compound represented by formula (2).

(1-3-1) Step (IB)

For step (IB) of the method for producing an alkane compound of the present disclosure, the explanation in "1-2: Method for Producing Alkene Compound" described above can be directly used.

(1-3-2) Step (IIB)

The alkene compound represented by formula (2) is obtained by step (IB) described above. At that time, the cycloalkane compound represented by formula (3) used in the reaction also remains. Accordingly, in general, a mixture comprising the alkene compound represented by formula (2) and the cycloalkane compound represented by formula (3) is obtained after step (IB).

After step (IB), the alkene compound represented by formula (2) and the cycloalkane compound represented by formula (3) can be separated and used in step (IIB); however, because, for example, their composition formulas are the same, and their molecular weights are close, it is often difficult to separate the alkene compound represented by formula (2) and the cycloalkane compound represented by formula (3).

For example, octafluoro-2-butene of formula (2), wherein $X^1$ and $X^2$ are fluorine atoms, and $R^1$ and $R^2$ are trifluoromethyl groups:

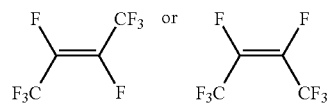

and octafluorocyclobutane (C318) of formula (3), wherein $R^3$, $R^4$, $R^5$, $R^6$, $R^7$, $R^8$, $R^9$, and $R^{10}$ are fluorine atoms:

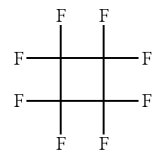 [SMILES: FC1(F)C(F)(F)C(F)(F)C1(F)F]

both have a composition formula of $C_4F_8$ and have close boiling points; thus, it is difficult to separate them.

In such a case, the mixture comprising the alkene compound represented by formula (2) and the cycloalkane compound represented by formula (3) obtained after step (IB) can be directly used as the raw material in step (IIB) without separation.

That is, the reaction can be allowed to proceed in the same manner as in "1-1: Method for Producing Alkane Compound from Alkene Compound" described above, except that a mixture (preferably mixed gas) containing the alkene compound represented by formula (2) and the cycloalkane compound represented by formula (3) is used instead of separately supplying the alkene compound represented by formula (2) and the cycloalkane compound represented by formula (3). Therefore, the explanation in "1-1: Method for Producing Alkane Compound from Alkene Compound" can be directly used, except that a mixture (preferably mixed gas) containing the alkene compound represented by formula (2) and the cycloalkane compound represented by formula (3) is used instead of separately supplying the alkene compound represented by formula (2) and the cycloalkane compound represented by formula (3).

2. Composition

The alkane compound represented by formula (1) can be obtained in the above manner. As described above, according to the production method of the present disclosure, the alkane compound represented by formula (1) can be obtained in such a manner that (S),(R) isomer, (R),(R) isomer, and (S),(S) isomer are co-produced. Therefore, according to the production method of the present disclosure, the alkane compound represented by formula (1) can be obtained as a composition comprising 3 alkane compounds represented by formulas (1A), (1B), and (1C):

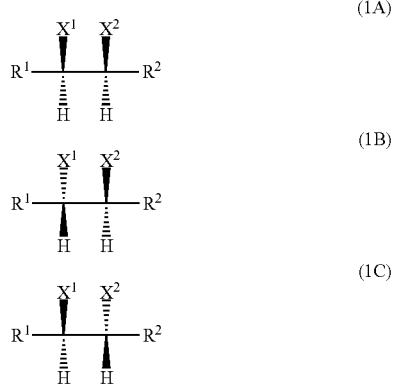

wherein $X^1$ and $X^2$ are the same or different and each is a halogen atom, and $R^1$ and $R^2$ are the same or different and each is an alkyl group or a fluoroalkyl group. The alkane compound represented by formula (1A) refers to (S), (R) isomer, the alkane compound represented by formula (1B) refers to (R), (R) isomer, and the alkane compound represented by formula (1C) refers to (S), (S) isomer.

In formulas (1A), (1B), and (1C), $X^1$, $X^2$, $R^1$, and $R^2$ may be those described above.

According to the production method of the present disclosure explained above, in the hydrogen addition reaction, syn addition and anti addition reactions proceed to the same extent; thus, the content of the alkane compound represented by formula (1A) in the composition of the present disclosure is likely to be almost the same as the total amount of the alkane compound represented by formula (1B) and the alkane compound represented by formula (1C). Further, since almost equal amounts of (R),(R) isomer and (S),(S) isomer are formed when the anti addition reaction proceeds, the content of the alkane compound represented by formula (1B) is likely to be almost the same as the content of the alkane compound represented by formula (1C). Therefore, the content of the alkane compound represented by formula (1A) is preferably 20 to 80 mol %, more preferably 30 to 75 mol %, and even more preferably 40 to 70 mol %, based on the total amount of the composition of the present disclosure, which is taken as 100 mol %. Further, the content of the alkane compound represented by formula (1B) is preferably 10 to 40 mol %, more preferably 12.5 to 35 mol %, and even more preferably 15 to 30 mol %. Moreover, the content of the alkane compound represented by formula (1C) is preferably 10 to 40 mol %, more preferably 12.5 to 35 mol %, and even more preferably 15 to 30 mol %. Each isomer is analyzed by gas chromatography (content) using a chiral column and NMR (structure determination).

According to the production method of the present disclosure, the alkane compound represented by formula (1) can be obtained at a high reaction conversion rate as well as a high yield and a high selectivity. Therefore, it is possible to reduce components other than the alkane compound represented by formula (1) in the composition, which can reduce the purification work to obtain the alkane compound represented by formula (1). Further, in step (IB), if it is difficult to separate the alkene compound represented by formula (2) and the cycloalkane compound represented by formula (3), even when the cycloalkane compound represented by formula (3) remains in the product, the alkane compound represented by formula (1) and the cycloalkane compound represented by formula (3) can be easily separated by a conventional method because they have different composition formulas.

The composition of the present disclosure described above can be effectively used for various applications, such as intermediates for organic synthesis, etching gases, and deposit gases. In particular, when the previously reported reaction is used for the composition of the present disclosure comprising the alkane compound represented by formula (1), alkyne compounds ($CF_3CECCF_3$ etc.) that can be effectively used for various applications, such as etching gases, cleaning gases, deposit gases, refrigerants, heat transfer media, and building blocks for organic synthesis, can also be synthesized.

Although the embodiments are described above, various changes in form and details can be made without departing from the spirit and scope of the claims.

The present disclosure includes the following configurations.

Item 1. A method for producing an alkane compound represented by formula (1):

$$R^1CHX^1CHX^2R^2 \qquad (1)$$

wherein $X^1$ and $X^2$ are the same or different and each is a halogen atom, and $R^1$ and $R^2$ are the same or different and each is an alkyl group or a fluoroalkyl group; the method comprising:

(IIA) reacting, in the presence of a catalyst and a cycloalkane compound represented by formula (3):

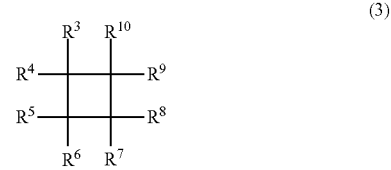

wherein $R^3$, $R^4$, $R^5$, $R^6$, $R^7$, $R^3$, $R^7$, and $R^{10}$ are the same or different and each is a halogen atom, an alkyl group, or a fluoroalkyl group; an alkene compound represented by formula (2):

wherein $X^1$, $X^2$, $R^1$, and $R^2$ are as defined above; and a hydrogen-containing gas to hydrogenate the alkene compound represented by formula (2).

Item 2. The production method according to Item 1, wherein the amount of the cycloalkane compound represented by formula (3) used in the hydrogenation step is 0.5 to 20 mol per mol of the alkene compound represented by formula (2).

Item 3. The production method according to Item 1 or 2, wherein the method comprises, before the hydrogenation step:

(IA) reacting a cycloalkane compound represented by formula (3):

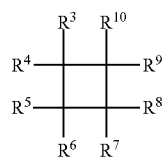

(3)

wherein $R^3$, $R^4$, $R^5$, $R^6$, $R^7$, $R^8$, $R^9$, and $R^{10}$ are as defined above, provided that when $R^1$ and $R^2$ in formula (1) are both alkyl groups, $R^3$, $R^4$, $R^5$, $R^6$, $R^7$, $R^8$, $R^9$, and $R^{10}$ are the same or different and each is a halogen atom or a fluoroalkyl group; and an alkene compound represented by formula (4):

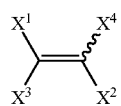

(4)

wherein $X^1$ and $X^2$ are as defined above, and $X^3$ and $X^4$ are the same or different and each is a halogen atom; to obtain an alkene compound represented by formula (2):

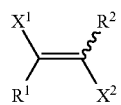

(2)

wherein $X^1$, $X^2$, $R^1$, and $R^2$ are as defined above.

Item 4. A method for producing an alkane compound represented by formula (1):

$$R^1 CHX^1 CHX^2 R^2 \quad (1)$$

wherein $X^1$ and $X^2$ are the same or different and each is a halogen atom, and $R^1$ and $R^2$ are the same or different and each is an alkyl group or a fluoroalkyl group; the method comprising:

(IB) reacting a cycloalkane compound represented by formula (3):

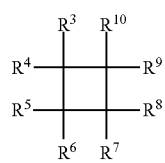

(3)

wherein $R^3$, $R^4$, $R^5$, $R^6$, $R^7$, $R^8$, $R^9$, and $R^{10}$ are the same or different and each is a halogen atom, an alkyl group, or a fluoroalkyl group, provided that when RE and $R^2$ in formula (1) are both alkyl groups, $R^3$, $R^4$, $R^5$, $R^6$, $R^7$, $R^8$, $R^9$, and $R^{10}$ are the same or different and each is a halogen atom or a fluoroalkyl group; and an alkene compound represented by formula (4):

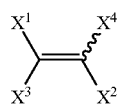

(4)

wherein $X^1$ and $X^2$ are as defined above, and $X^3$ and $X^4$ are the same or different and each is a halogen atom; to obtain a mixture comprising a cycloalkene compound represented by formula (2):

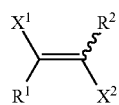

(2)

wherein $X^1$, $X^2$, $R^1$, and $R^2$ are as defined above; and the cycloalkane compound represented by formula (3); and (IIB) reacting the mixture obtained in step (IB) and a hydrogen-containing gas in the presence of a catalyst to hydrogenate the cycloalkene compound represented by formula (2).

Item 5. The production method according to Item 4, wherein in the hydrogenation step, the cycloalkane compound represented by formula (3) used as a raw material in the mixture is contained in an amount of 0.5 to 20 mol per mol of the alkene compound represented by formula (2).

Item 6. The production method according to any one of Items 1 to 5, wherein the hydrogenation step is performed in a gas phase.

Item 7. The production method according to any one of Items 1 to 6, wherein the alkane compound represented by formula (1) to be produced comprises 3 alkane compounds represented by formulas (1A), (1B), and (1C):

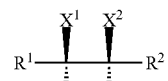

(1A)

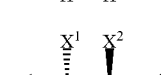

(1B)

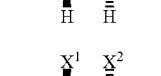

(1C)

wherein $X^1$, $X^2$, $R^1$, and $R^2$ are as defined above.

Item 8. The production method according to Item 7, wherein 20 to 80 mol % of the alkane compound represented by formula (1A), 10 to 40 mol % of the alkane compound represented by formula (1B), and 10 to 40 mol % of the alkane compound represented by formula (10) are obtained based on the total amount of a product obtained by the hydrogenation step, which is taken as 100 mol %.

Item 9. A composition comprising 3 alkane compounds represented by formulas (1A), (1B), and (1C):

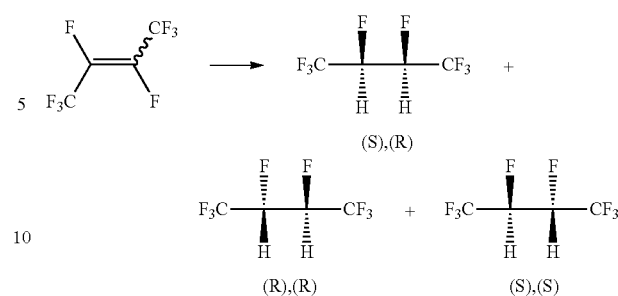

(1A)

(1B)

(1C)

wherein $X^1$ and $X^2$ are the same or different and each is a halogen atom, and $R^1$ and $R^2$ are the same or different and each is an alkyl group or a fluoroalkyl group; and
the alkane compound represented by formula (1A) being contained in an amount of 20 to 80 mol %, the alkane compound represented by formula (1B) being contained in an amount of 10 to 40 mol %, and the alkane compound represented by formula (1C) being contained in an amount of 10 to 40 mol %, based on the total amount of the composition, which is taken as 100 mol %.

Item 10. The composition according to Item 9, which is used as an intermediate for organic synthesis, an etching gas, or a deposit gas.

EXAMPLES

The features of the present disclosure are clarified below while showing Examples. The present disclosure is not limited to these Examples.

In the methods for producing an alkane compound of Examples 1 to 5 and Comparative Examples 1 to 3, the raw material compound was a halogenated butane compound represented by formula (2A) wherein $X^1$ and $X^2$ are fluorine atoms, and $R^1$ and $R^2$ are trifluoromethyl groups, and an alkane compound was obtained by a hydrogen addition reaction according to the following reaction formula:

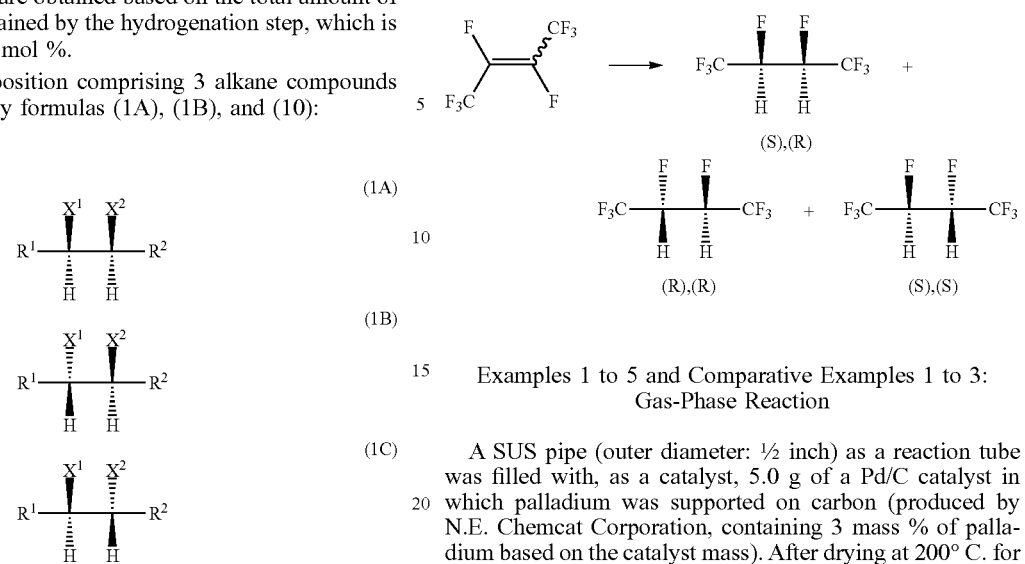

Examples 1 to 5 and Comparative Examples 1 to 3: Gas-Phase Reaction

A SUS pipe (outer diameter: ½ inch) as a reaction tube was filled with, as a catalyst, 5.0 g of a Pd/C catalyst in which palladium was supported on carbon (produced by N.E. Chemcat Corporation, containing 3 mass % of palladium based on the catalyst mass). After drying at 200° C. for 2 hours in a nitrogen atmosphere, octafluoro-2-butene (raw material compound; a mixture of cis- and trans-isomers) was allowed to flow through the reaction tube at normal pressure so that the contact time (W/F) of octafluoro-2-butene (raw material compound) and the Pd/C catalyst was 1.7 to 9.3 g·sec/cc. Octafluorocyclobutane (C318) was allowed to flow so that the molar ratio of octafluorocyclobutane (C318) and octafluoro-2-butene (raw material compound) was 0, 1, or 4 (a molar ratio of 0 means that C318 is not allowed to flow). Further, a hydrogen gas to be reacted was allowed to flow.

The reaction was allowed to proceed by a gas-phase continuous flow process.

The reaction tube was heated at 70 to 100° C. to start the hydrogen addition reaction.

The molar ratio ($H_2$/octafluoro-2-butene ratio) of the hydrogen gas to be brought into contact with octafluoro-2-butene (raw material compound) was adjusted to 1.1, and the distillate that passed through the abatement tower was collected one hour after the start of the reaction. However, in Comparative Example 3, a mixed gas diluted with a nitrogen gas so that the molar ratio ($N_2/H_2$) of nitrogen and hydrogen was 4 was used in place of the hydrogen gas.

After that, mass spectrometry was performed by gas chromatography/mass spectrometry (GC/MS) using a gas chromatograph (produced by Shimadzu Corporation, trade name: "GC-2014"). Structural analysis using NMR spectra was performed using NMR (produced by JEOL Ltd., trade name: "400YH"). From the results of mass spectrometry and structural analysis, it was confirmed that $CF_3CHFCHFCF_3$ was produced as a target compound. The results are shown in Table 1.

TABLE 1

| | Example | | | | | Comparative Example | | |
|---|---|---|---|---|---|---|---|---|
| | 1 | 2 | 3 | 4 | 5 | 1 | 2 | 3 |
| Temperature (° C.) | 70 | 70 | 70 | 100 | 70 | 80 | 70 | 70 |
| W/F (g · sec/cc) | 5.7 | 3.2 | 1.7 | 5.7 | 1.7 | 9.3 | 9.3 | 3 |
| Molar ratio C318/$CF_3CF=CFCF_3$ | 4 | 4 | 4 | 4 | 1 | No C318 | No C318 | No C318 |
| Molar ratio $H_2$/$CF_3CF=CFCF_3$ | 1.1 | 1.1 | 1.1 | 1.1 | 1.1 | 1.1 | 1.1 | 1.1 |

TABLE 1-continued

|  | Example | | | | | Comparative Example | | |
|---|---|---|---|---|---|---|---|---|
|  | 1 | 2 | 3 | 4 | 5 | 1 | 2 | 3 |
| Conversion rate (mol %) | 92.7 | 100.0 | 100.0 | 97.6 | 100.0 | 100.0 | 100.0 | 100.0 |
| Selectivity (mol %) | | | | | | | | |
| $CF_3CHFCHFCF_3$ | 98.1 | 98.1 | 98.0 | 98.4 | 94.7 | 98.7 | 99.1 | 98.7 |
| (S),(R) isomer | 51.4 | 54.2 | 54.1 | 50.8 | 51.2 | 89.8 | 89.5 | 90.6 |
| (R),(R) isomer | 20.9 | 20.0 | 19.5 | 20.1 | 20.0 | 1.8 | 1.6 | 0.0 |
| (S),(S) isomer | 25.8 | 23.9 | 24.4 | 27.5 | 23.5 | 7.1 | 8.0 | 8.1 |
| Others | 1.9 | 1.9 | 2.0 | 1.6 | 5.3 | 1.3 | 0.9 | 1.3 |

The invention claimed is:

1. A method for producing an alkane compound represented by formula (1):

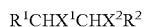

wherein $X^1$ and $X^2$ are the same or different and each is a fluorine atom, and $R^1$ and $R^2$ are the same or different and each is an alkyl group or a fluoroalkyl group; the method comprising:

(IIA) reacting, in the presence of a catalyst and a cycloalkane compound, an alkene compound and a hydrogen-containing gas to hydrogenate the alkene compound, wherein the cycloalkane compound is represented by formula (3):

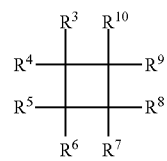

wherein $R^3$, $R^4$, $R^5$, $R^6$, $R^7$, $R^8$, $R^9$, and $R^{10}$ are the same and each is a fluorine atom, or a fluoroalkyl group, and wherein the alkene compound is represented by formula (2):

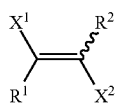

wherein $X^1$, $X^2$, $R^1$, and $R^2$ are as defined above.

2. The production method according to claim 1, wherein the amount of the cycloalkane compound represented by formula (3) used in the hydrogenation step is 0.5 to 20 mol per mol of the alkene compound represented by formula (2).

3. The production method according to claim 1, wherein the method comprises, before the hydrogenation step:

(IA) reacting a cycloalkane compound represented by formula (3):

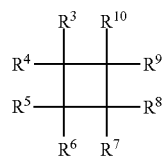

wherein $R^3$, $R^4$, $R^5$, $R^6$, $R^7$, $R^8$, $R^9$, and $R^{10}$ are as defined above; and an alkene compound represented by formula (4):

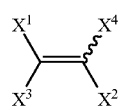

wherein $X^1$ and $X^2$ are as defined above, and $X^3$ and $X^4$ are the same or different and each is a fluorine atom; to obtain an alkene compound represented by formula (2):

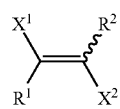

wherein $X^1$, $X^2$, $R^1$, and $R^2$ are as defined above.

4. A method for producing an alkane compound represented by formula (1):

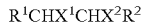

wherein $X^1$ and $X^2$ are the same or different and each is a fluorine atom, and $R^1$ and $R^2$ are the same or different and each is an alkyl group or a fluoroalkyl group; the method comprising:

(IB) reacting a cycloalkane compound represented by formula (3):

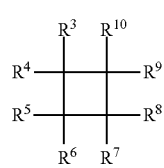

wherein $R^3$, $R^4$, $R^5$, $R^6$, $R^7$, $R^8$, $R^9$, and $R^{10}$ are the same and each is a fluorine atom, or a fluoroalkyl group; and an alkene compound represented by formula (4):

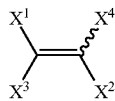  (4)

wherein $X^1$ and $X^2$ are as defined above, and $X^3$ and $X^4$ are the same or different and each is a fluorine atom; to obtain a mixture comprising an alkene compound represented by formula (2):

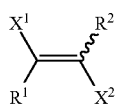  (2)

wherein $X^1$, $X^2$, $R^1$, and $R^2$ are as defined above; and the cycloalkane compound represented by formula (3); and
(IIB) reacting the mixture obtained in step (IB) and a hydrogen-containing gas in the presence of a catalyst to hydrogenate the alkene compound represented by formula (2).

5. The production method according to claim 4, wherein in the hydrogenation step, the cycloalkane compound represented by formula (3) used as a raw material in the mixture is contained in an amount of 0.5 to 20 mol per mol of the alkene compound represented by formula (2).

6. The production method according to claim 1, wherein the hydrogenation step is performed in a gas phase.

7. The production method according to claim 1, wherein the alkane compound represented by formula (1) to be produced comprises 3 alkane compounds represented by formulas (1A), (1B), and (1C):

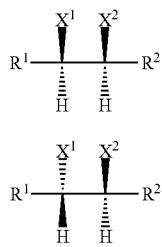

wherein $X^1$, $X^2$, $R^1$, and $R^2$ are as defined above.

8. The production method according to claim 7, wherein 20 to 80 mol % of the alkane compound represented by formula (1A), 10 to 40 mol % of the alkane compound represented by formula (1B), and 10 to 40 mol % of the alkane compound represented by formula (1C) are obtained based on the total amount of a product obtained by the hydrogenation step, which is taken as 100 mol %.

9. The production method according to claim 4, wherein the hydrogenation step is performed in a gas phase.

10. The production method according to claim 4, wherein the alkane compound represented by formula (1) to be produced comprises 3 alkane compounds represented by formulas (1A), (1B), and (1C):

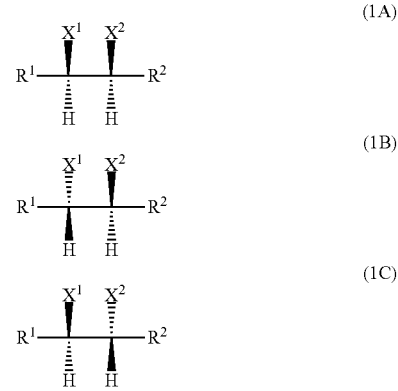

wherein $X^1$, $X^2$, $R^1$, and $R^2$ are as defined above.

11. The production method according to claim 10, wherein 20 to 80 mol % of the alkane compound represented by formula (1A), 10 to 40 mol % of the alkane compound represented by formula (1B), and 10 to 40 mol % of the alkane compound represented by formula (1C) are obtained based on the total amount of a product obtained by the hydrogenation step, which is taken as 100 mol %.

* * * * *